US006638918B2

(12) United States Patent
Davison et al.

(10) Patent No.: US 6,638,918 B2
(45) Date of Patent: Oct. 28, 2003

(54) CHITOSAN COMPOSITIONS

(75) Inventors: Gordon Robert Davison, Warfield (GB); Axel Konig, Wemmel (BE); Clyde Gibbons, Staines (GB); Mark Brian Ripley, Twickenham (GB); Neil Archibald MacGilp, Bramley (GB); Georgina Lyndsey Claire Milich, Harefield (GB); Emma Louise Pretswell, Bracknell (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/280,617

(22) Filed: Oct. 25, 2002

(65) Prior Publication Data

US 2003/0104020 A1 Jun. 5, 2003

(30) Foreign Application Priority Data

Nov. 9, 2001 (GB) .............................. 0126923

(51) Int. Cl.$^7$ ......................... A01N 43/04; C08B 37/00
(52) U.S. Cl. .................. 514/55; 536/20; 536/123.1
(58) Field of Search .............. 514/55; 536/20, 536/123.1

(56) References Cited

U.S. PATENT DOCUMENTS 4,983,304 A   1/1991   Tsugita et al.

FOREIGN PATENT DOCUMENTS

| DE | 10014529 | * | 9/2001 | ............ A61K/7/32 |
| EP | 1 092 425 | A1 | 4/2001 | |
| JP | 9 249541 | A | 9/1997 | |
| WO | WO 00/47177 | A1 | 8/2000 | |
| WO | WO 00/54733 | A2 | 9/2000 | |
| WO | WO 01/10421 | A1 | 2/2001 | |
| WO | WO 01/10421 | * | 2/2001 | ............ A61K/9/70 |
| WO | WO 01/19187 | A1 | 3/2001 | |
| WO | WO 01/32751 | A1 | 5/2001 | |
| WO | WO 01/32751 | * | 5/2001 | ............ C08J/3/14 |
| WO | WO 01/87988 | A1 | 11/2001 | |
| WO | WO 02/077358 | A1 | 10/2002 | |

OTHER PUBLICATIONS

Bodek, K. H. et al., Protolytic and Complexing Properties of Microcrystalline Chitosan with Co(II), Zn(II), and Cu(II) Ions, 2296 Journal of Applied Polymer Science 57 (1995) Aug. 1, No. 5, pp. 645–49.

* cited by examiner

*Primary Examiner*—Samuel Barts
*Assistant Examiner*—Ganapathy Krishnan
(74) *Attorney, Agent, or Firm*—Peter D. Meyer

(57) ABSTRACT

Compositions comprising chitosan in the form of a network of nano-sized fibres. There is also provided a process for making such compositions. The compositions have improved solubility and activity. The compositions are useful in hair care, skin care, odour control, wound care, blood management, sanitary compositions, oral care, film formation, hard surface treatment, fabric treatment, release of hydrophobic or hydrophilic materials, plant care, water purification and drug delivery.

20 Claims, No Drawings

CHITOSAN COMPOSITIONS

TECHNICAL FIELD

The present invention relates to chitosan compositions, especially to chitosan compositions comprising nano-sized chitosan. The compositions present improved bioactivity, solubility and other properties over traditional chitosan. The invention also relates to a process for making the compositions and uses thereof.

BACKGROUND OF THE INVENTION

Chitin is the main constituent in the shells of crustaceans and is the most abundant naturally occurring biopolymer other than cellulose. Chitosan is derived from chitin and can be formed by deacetylation of chitin. Chitosan is commercially available in a wide variety of molecular weights (e.g., 10–1,000 kDa) and usually has a degree of deacetylation ranging between 70% and 90%. Chitosan is used for a wide variety of purposes including plant care, cosmetics additives, food and nutrition supplements and medical care.

The properties and applications of chitosan are strongly linked to its morphology, structure and size and these are directly related to the process used for obtaining chitosan. For reasons of clarity, the chitosan obtained as the initial product from chitin will be referred to herein as primary chitosan and the chitosan obtained from the subsequent treatment of this primary chitosan will be referred as modified chitosan.

Traditional primary or modified chitosan has a limited solubility, limited developed internal surface, large particle size, low water retention value and limited bio-availability. Traditional chitosan is usually semi-crystalline and only soluble in acidic medium, typically in a pH range from 1 to 5; this limits homogenous formulation. Another drawback of traditional chitosan being that it does not present optimum biological activity, mainly due to its dense semi-crystalline nature in solid form.

Processes for obtaining modified chitosan are known in the art. For instance, copending U.S. Ser. No. 01/15182 describes a process for the production of microcrystalline chitosan. The process involves the dissolution of primary chitosan in an aqueous acidic solution followed by the neutralization of the solution, producing an aqueous gel containing precipitated microcrystalline chitosan. According to U.S. Ser. No. 01/15182 the microcrystalline chitosan particles range in size from 2 to 20 $\mu$m and have a water solubility of at least 90% at pH of 6 after 24 hours.

For some applications it is preferred to use nanoparticulate chitosan, not only because it is more readily active for biological use but also because it presents greater solubility and a more open and finely divided architecture. Processes for obtaining nanoparticulate chitosan are described in several prior art documents. For instance, WO 01/32751 describes a process for producing nanoparticulate chitosan, with particle diameters in the range from 10 to 1,000 nm. According to the prior art invention, the chitosan is dissolved in an acidic aqueous medium and the pH of the solution is raised in the presence of a surface modifier to such an extent that the chitosan is precipitated. One of the drawbacks of this process is that the nanoparticulate chitosan has a high content of surface modifier. This can be detrimental for some applications such as pharmaceutical and cosmetic applications because the surface modifier can irritate human tissues and for plant applications because the surface modifier can be phytotoxic for plants. Furthermore, the nanoparticulate chitosan obtained according to this process can have its activity reduced because the surface active modifier can render the nanoparticulate chitosan less readily available, this is important in the case of anti-microbial (anti-bacterial, anti-fungal and anti-viral) applications.

WO 00/47177 discloses a process for producing nanoparticulate chitosan, with particle diameters in the range from 10 to 300 nm. A gas anti-solvent (GAS) process is preferably used wherein the chitosan is dissolved in solvent and a gas ($CO_2$) miscible with the solvent and immiscible with chitosan, to reduce the bulk density of the solution and hence cause a reduction of the solubility limits of the chitosan in the expanded solution and thereby promoting the precipitation of chitosan. The process requires the use of high pressures and temperatures; also the recovery of precipitate from the pressurized vessel is a complex operation. This process may be convenient for lab or small scale operation, however, the scale-up of the process raises considerable problems. The resulting nanoparticulate chitosan may also retain solvent impurities giving rise to similar drawbacks as discussed herein above in relation to WO 01/32751.

In view of the above discussion, there is a need for an improved form of modified chitosan which is soluble over a wider range of pH, with a suitable viscosity, with improved bioactivity and other properties and which permits greater flexibility in formulation. There is also a need for an easy and simple process to produce nanoparticulate chitosan, free from surface modifier and with improved activity and greater flexibility in use.

SUMMARY OF THE INVENTION

The present invention relates in part to compositions comprising pure nanoparticulate chitosan, i.e. which can be made free from surface modifiers or organic solvents, wherein the chitosan presents a special morphology which allows for the compositions to have a high degree of flexibility in formulation and for the chitosan to have an increased activity. The term chitosan as used herein not only includes the natural polysaccharide $\beta$-1,4-poly-D-glucosamine obtained by deacetylation of chitin or by direct isolation from fungi but also includes synthetically produced $\beta$-1,4-poly-D-glucosamines and derivatives thereof of equivalent structure to chitosan.

According to a first aspect of the invention, there is provided a composition comprising chitosan in the form of a network of nano-sized fibres. Preferably, the fibre network has an interstitial space as determined for example by cryogenic transmission electron microscopic (cryo-TEM) imaging of at least about 60%, preferably at least about 80%, more preferably at least about 88% and especially at least about 89%. The network of nano-sized fibres is very open and very accessible. It should be understood that most of the chitosan will be in the form of a network of nano-sized fibres, however, a minor portion of the chitosan, preferably less than about 10% and more preferably less than about 5%, could be in a different form. The composition has an improved solubility over traditional forms of chitosan and is capable of producing fully homogeneous formulations in the critically important physiological pH region, for example from about 5 to about 7. As consequence, it can be used in a large number of applications. Additionally, the chitosan in the form of a network of fibres as described herein presents an increased activity. It presents superior bioactivity for plant and crop applications, enhanced delivery of chelated nutrient metals for plant care, improved efficacy as soil enhancer/conditioner, improved sebum/dandruff control in skin and hair care products, greater anti-microbiological efficacy, enhanced flocculation and absorbency efficacy, improved efficacy in odour control, oral care, etc.

By interstitial space is herein meant the average percent of open space in a two-dimensional projection of the three-dimensional chitosan fibre network. Open space is the space between the fibres of the network and is generally occupied by water or other solvent. The interstitial space is preferably measured by direct imaging cryo-TEM. A sample of the chitosan composition is diluted to 0.5% by adding water to the composition using a Vortex mixer table-top model (#12-810) (Fisher Scientific Company, Pittsburgh, Pa.) for 10 s followed by sonication using a tip sonicator Branson Sonifier S12 (Branson Sonic Power Co., Danbery, Conn.) for 10 s at 50 watts to fully disperse the sample. A 3 μl drop of the sample solution is placed on a carbon-coated lacey polymer support film mounted on a standard 300 mesh TEM grid. The drop is blotted with filter paper until it is reduced to a thin film (10–200 nm) spanning the holes (2–8 μm.) of the support film. The sample is then vitrified (in a controlled environment vitrification system (CEVS) as described in "Controlled Environment Vitrification Technique", J. Electron Microsc. Tech., 1988, 10, 87–111 by rapidly plunging it through a synchronous shutter at the bottom of the CEVS into liquid ethane at its freezing point. The vitreous specimen is then transferred under liquid nitrogen into a Philips (FEI) CM120 transmission electron microscope for imaging. The microscope is operated at an accelerating voltage of 120 kV. The temperature of the sample is kept below –180° C. throughout the examination. The sample is examined in the low-dose imaging mode to minimize electron-beam radiation damage. Images are recorded digitally by a Gatan 791 MultiScan CCD camera using Digital Micrograph 3.3 software. Images are exported as 8-bit TIFF images (256 grey scale, where in 0 corresponds to black and 255 to white). After the image is obtained Metamorph 4.5 Universal Imaging Corporation software is used to determine the interstitial space. A region of the image containing discernible individual chitosan fibres and free of other inclusions such as frost, is manually selected and the background is flattened by standard protocols to reduce shading effects occurred during data acquisition. Digital contrast of regions is increased consistently, by adjusting Metamorph Contrast function from 50 to 62. A threshold value (typically 137) is set up by using an Auto Threshold for dark objects (chitosan fibres) function provided in Metamorph imaging software. The amount of chitosan area (grey values of less than 137) and interstitial space (grey values greater than 137) are calculated as a percentage of total region area. It should be noted that the calculated interstitial space may vary slightly from region to region, a slight variation herein being considered a variation of less than 15%, preferably less that 10% and more preferably less than 5% when areas of comparable thickness (as given by the average grey value of the image raw data) and free of inclusions are measured at different locations of the same sample grid. If necessary, sufficient replicates are undertaken to establish confidence limits.

In a preferred embodiment, the nano-sized chitosan fibres have on average a length of from about 5 to about 200 nm, preferably from about 50 to about 100 nm and more preferably from about 55 to about 95 nm, a width of from about 5 to about 30 nm, preferably from about 7 to about 20 nm and more preferably from about 12 to about 18 nm, and a thickness of from about 0.1 to about 10 nm, preferably from about 1 to about 8 nm and more preferably from about 2 to about 6 nm. The fibre dimensions are again measured from the cryo-TEM images. As in the case of the interstitial space, the measurement of fibre average dimensions may vary slightly between samples and if necessary, sufficient replicates are undertaken to establish confidence limits.

Thus, according to a second aspect of the invention, there is provided a composition comprising chitosan in the form of a network of nano-sized fibres having on average a length of from about 5 to about 200 nm, preferably form about 50 to about 100 nm and more preferably from about 55 to about 95 nm, a width of from about 5 to about 30 nm, preferably form about 7 to about 20 nm and more preferably from about 12 to about 18 nm, and a thickness of from about 0.1 to about 10 nm, preferably from about 1 to about 8 nm and more preferably from about 2 to about 6 nm. This composition has an improved solubility over traditional forms of nanoparticulate chitosan and permits its use in a large number of applications. Additionally, the chitosan presents an increased activity.

The chitosan compositions of the invention are also characterized by having excellent water-retention value (WRV). In a preferred embodiment, the network of nano-sized chitosan fibres has a water retention value of at least about 3000%, preferably at least about 3500%, more preferably at least about 4000% and even more preferably at least about 4500%.

Water retention value of the chitosan is herein calculated by firstly fully hydrating the chitosan in an excess of water, then centrifuging the chitosan composition to remove the supernatant water followed by drying. The measured weight loss after drying is used to calculate the WRV of the material. The method is as follows: firstly, the fully hydrated chitosan composition is stirred to ensure that it is homogeneous. Then a 10 grams sample is placed in a plastic centrifuge tube and an initial spin is carried out using a Beckman Avanti 30 centrifuge at 4400 rpm for 30 minutes (2087G) to remove the majority of water. The water is decanted and the sample retained for further analysis. A glass microfibre filter paper (Whatman GF/B, Cat. No: 1821-025) is placed on the top of a plastic filter tube, 5 grams of the initially spun chitosan is placed onto the filter paper. The sample is further centrifuged at 5000 rpm for 10 minutes (2683G). 2 g of the resulting material (taken without scratching the bottom filter) are placed into a metallic dish of known weight. The metallic dish is placed in an oven at 120° C. for at least 4 hours and up to 20 hours. Afterwards, the dish is removed from the oven and allowed to cool in a dessicator. Finally, the dish containing the dried chitosan is weighed and the water retention value (WRV) calculated as follows:

$$WRV = \frac{CentrifugedSampleWt(g) - DriedSampleWt(g)}{DriedSampleWt(g)} \times 100\%$$

According to another aspect of the invention, therefore, there is provided a composition comprising chitosan in the form of a network of nano-sized fibres and wherein the chitosan has a water retention value of at least about 3000%, preferably at least about 3500%, more preferably at least about 4000% and even more preferably at least about 4500%.

The chitosan compositions herein are also characterized by having a high chitosan surface area, a low degree of crystallinity and an extended pH range of solubility. In particular, the chitosan preferably has a surface area of at least about 100 m$^2$/g, a degree of crystallinity below about 1% and is soluble in aqueous solutions having a pH between about 1 and about 6.3.

Thus, according to a further aspect of the invention, there is provided a composition comprising chitosan in the form of a network of nano-sized fibres and wherein the chitosan has a surface area of at least about 100 m$^2$/g, a degree of crystallinity below about 1% and is soluble in substantially pure aqueous solutions having a pH between about 1 and about 6.3.

The degree of crystallinity of the chitosan compositions is measured herein by X-ray diffraction. A Scintag X1 (MV28423, Serial #218–295, 0336) powder x-ray diffractometer is used. The generator is operated at 40 kV/45 mA, powering a normal focus copper x-ray tube. A solid-state detector is used. The x-ray beam is collimated using incident beam slits of 2 and 4 mm and diffracted beam slits of 0.5 and 0.2 mm. Data are collected using a step-scan mode from 2 to 60 θ at 2.5 seconds/step and a step size of 0.04°. The degree of crystallinity is calculated as the ratio of the area of the crystalline peaks to the sum of the areas of the crystalline peaks and the amorphous region from 7 to 49 θ. Results reported are generally based on the average of two calculations for each analysis or sufficient to ensure reproducibility.

The surface area of the chitosan is measured by Brunauer-Emmet-Teller (BET) surface area measurement technique. Before measurement wet samples are dried by Critical Point Drying (CPD). The CPD method is as follows:

Firstly 0.5–1 cm$^3$ of a wet chitosan sample is placed in a syringe with 5 ml 70% ethanol and shaken well to mix. The material is then filtered over a 2 μm Millipore filter. This procedure is repeated with 90% and then 100% (absolute) ethanol. Next the sample is transferred to a CPD holder and then to a CPD apparatus (Agar Scientific Jumbo Critical Point Drier, Model No. B7010A). The sample is flushed with $CO_2$ to remove ethanol and then maintained at pressure for at least one hour. This procedure is repeated twice. The sample is then flushed with $CO_2$ and the temperature is increased until the critical point (31° C./76 bar) is reached. The CPD is then returned to atmospheric pressure slowly to allow the $CO_2$ to evaporate. Each run takes about 30 min preparation time and 2.5 hrs CPD time. Each run yields between 1.0 and 0.25 g of dry material.

The samples are analysed as submitted from the CPD method (care is taken not to crush them). A small amount is weighed into a sample tube. The tube is then attached to an outgassing station and left under vacuum for 18 hrs at room temperature. This is to ensure that the surface is clean and solvent-free to allow nitrogen adsorption to occur. After outgassing, the samples are re-weighed and then transferred to a Quantachrome Autosorb-1 instrument to measure the quantity of gas adsorbed onto or desorbed from the surface at the equilibrium pressure by the static volumetric method. The surface area is determined using nitrogen as the adsorbate at 77.1K.

The compositions comprising a network of nano-sized chitosan fibres can be in the form of a suspension, dispersion or paste. The suspension, dispersion or paste preferably comprises from about 0.1% to about 15%, preferably from about 1% to about 10% by weight of chitosan, this chitosan content being preferred from the viewpoint of forming the desired nanoparticle structure. The compositions can be diluted if required for specific applications.

According to another aspect of the invention, there is provided a process for making the chitosan compositions. The process involves the steps of forming an aqueous solution of chitosan by dissolving chitosan in an aqueous acidic solution followed by partially neutralizing said solution by means of a neutralizing agent. The neutralization is preferably carried out to the point at which the chitosan just precipitates to form a suspension and thereafter the suspension is homogenized by subjecting it to high shear. The precipitated chitosan is then preferably washed with de-ionized water to a conductivity below 1.6 milliSiemens/cm$^2$. The resulting chitosan aqueous suspension is pure chitosan with a maximum salt concentration of less than 5%, preferably less than 2% by weight of chitosan.

The starting chitosan material can be any commercially available chitosan. Suitable chitosan sources may be those derived from shellfish, insects or may be fungally derived. Preferred for use herein are chitosan materials having a molecular weight from about 10.000 to about 500.000 Da. Alternatively, high molecular weight chitosans can be left in the acid solution for a length of time sufficient to reduce the molecular weight thereof to the preferred range by acid catalysed hydrolysis.

The acid used to dissolve the chitosan is preferably selected from acetic, maleic, citric, lactic, salicylic, hydrochloric acid and mixtures thereof. Preferred for use herein are lactic acid and hydrochloric acid; especially the latest for obtaining chitosan compositions in which the chitosan has a high water retention value. The concentration of chitosan in the dilute acidic solution is preferably from about 0.1% to about 10%, more preferably from about 0.5% to about 2% by weight, these values being preferred from the process viewpoint, in order to provide a solution with the right consistency and with the required degree of constraint for producing the desired final chitosan suspension. The pH is preferably in the range from about 1 to about 5. Crystallization inhibitors, as for example diethylene triamine penta (methyl phosphonic) acid, can be added to the solution to avoid premature seed formation which can become crystal growth centres.

The resulting acidic chitosan solution can be optionally filtered to remove insoluble impurities. The neutralization step is carried out by means of a neutralizing agent. Preferred for use herein as neutralizing agent is an aqueous solution comprising from about 0.01% to about 4%, preferably from about 0.05% to about 3% by weight of metal hydroxide, ammonium hydroxide, organic bases such as monoethanolamine or triethanolamine or mixtures thereof. Sodium hydroxide and ammonium hydroxide are preferred for use herein from the cost viewpoint.

In a preferred process embodiment, the solution is partially neutralized up to the point in which the solution becomes a precipitate suspension, the pH preferably being in the range of from about 6.5 to about 7.5, more preferably from about 6.7 to about 7.1. At this point the solution appearance changes from clear to opaque and takes the form of a milky dispersion. Preferably, the partial neutralization is carried out in two sub-stages, wherein the first sub-stage involve neutralization with a relatively concentrated neutralizing agent up to a pH from about 4 to about 6.7, preferably from about 5.3 to about 5.8, the second sub-stage involves the use of a relatively dilute neutralizing agent, preferably the neutralizing agent being diluted by a factor of at least 5, preferably at least 9 as compared with the neutralization agent used in the first sub-stage.

Afterwards, the suspension is subject to intensive homogenisation, during which it is preferred that the system has a Reynolds number of from about 8,000 to about 20,000, preferably from about 12,000 to about 16,000.

Reynolds number is defined by the following equation:

$$Re = \frac{\rho D^2 N}{\mu}$$

wherein ρ (kg/m³) is the density of the suspension, D is the diameter of the impeller (m), N is the rotation speed of the impeller (s⁻¹) and μ is the apparent viscosity of the suspension (N s/m²).

It is believed that the morphology of the modified chitosan produced using this process is to a great extent determined by the mixing regimen and more specifically by the shear at which the solution is subjected after neutralization. It has been found that in order to obtain chitosan with optimum morphology and performance characteristics the precipitate suspension formed should be homogenized by subjecting it to a high shear. By high shear is generally meant a shear sufficiently high to obtain the requisite network of nano-sized fibres as described hereinabove. This high shear can be achieved using any kind of high shear mixing operation for example by stirring using an impeller having a speed of rotation of at least about 500 rpm, preferably at least about 600 rpm. It is also preferred that the system has an average shear rate of at least about 80 s⁻¹, preferably at least about 100 s⁻¹. Average shear rate is given by the following equation:

$$\Gamma_{av} = kN$$

wherein $\Gamma_{av}$ (s⁻¹) is the average angular shear rate for the mixing, k is a proportionality constant which is a function of the type of impeller and the vessel configuration and N (s⁻¹) is the speed of the agitator. It has been found that for the majority of practical systems k lies in the range form about 10 to about 13. The above equation for average shear rate is defined in "Agitation of Non-Newtonian fluids" Metzner and Otto, AIChE Journal, 1957, Vol 3, No. 1, pages 3–10.

It is also preferred that the impeller has a tip speed of at least about 4 m/s, as given by the following equation:

$$\text{Tip speed} = (\pi ND)$$

wherein D is the diameter of the impeller in meters.

Preferably, the mixing is carried out mainly under laminar regime conditions and using an impeller such that the ratio of the diameter of the impeller to the diameter of the mixing vessel is at least about 0.4, preferably at least about 0.5 and especially about 0.55, this being preferred from the viewpoint of obtaining a homogeneous suspension.

Preferably, the suspension is homogenized at a speed of at least about 500 rpm for a period of at least about 10 s, preferably at least about 15 min.

After the suspension has been homogenized the process can be continued by further neutralising the homogenized suspension by means of an aqueous solution of a neutralizing agent comprising from about 0.01% to about 1%, preferably from about 0.05% to about 0.5% by weight of metal hydroxide, ammonium hydroxide or mixtures thereof, and thereafter further homogenizing the neutralized suspension under a second application of high shear, preferably using a stirring speed of at least about 500 rpm, more preferably at least about 600 rpm. This high shear can be achieved by similar means to those described hereinabove. Without being bound by theory, it is believed that in this part of the process not only the shear has a strong influence on the output of the process but also the concentration of the neutralizing agent.

In a preferred process embodiment, the solution is further neutralized up to the point in which the suspension reaches a pH of from about 7.0 to about 7.8, preferably from about 7.2 to about 7.6. Afterwards, the suspension is homogenized, during which it is preferred that the system has a Reynolds number of from about 18,000 to about 35,000, preferably from about 22,000 to about 26,000. This homogenisation is carried out at high shear preferably for a period of at least about 10 s and more preferably at least about 15 min. Finally, the suspension can be purified by washing with deionised water in for example a filter bed to remove water-soluble impurities. The compositions can also be dried by means of a drying technique which preserves the structure of the chitosan, such as for example critical point drying technique as described hereinabove.

According to other aspects of the invention, there are provided uses of the chitosan compositions in different applications, such as hair care, skin care, personal cleansing, odour control, wound care, blood management, oral care, film formation, controlled release of hydrophobic or hydrophilic materials, hard surface, fabric treatment, plant care, seed, grain, fruit and food protection, water purification and drug delivery.

DETAILED DESCRIPTION OF THE INVENTION

The present invention envisages chitosan compositions wherein the chitosan is in the form of a network of nano-sized fibres. These compositions have superior properties over other known forms of primary chitosan and modified chitosans. The invention also envisages a process for making the compositions and uses of said compositions.

The chitosan compositions have improved activity and can be used in a number of different applications. The compositions provide hair care benefits when formulated into products such as shampoos, conditioners, hairsprays, styling mouses and gels, hair tonics and hair colorants, especially anti-dandruff benefits and reduction of hair damage caused by the process of hair bleaching, permanent waving or coloration. Additionally, the compositions provide scalp benefits and conditioning properties such as softening, manageability and stylising of the hair. It is believed that the compositions reduce hair damage during bleaching, permanent waving and coloration by chelation of copper and other transition metals with chitosan, reducing the amount of free-radicals generated with oxidant agents. It has surprisingly been found that the minimum concentration of the chitosan, in the form described herein above, needed to inhibit *Malassezia furfur* (a yeast implicated in dandruff) and therefore to provide anti-dandruff benefits is significantly lower than that required for other known chitosans and modified chitosans and for other known anti-dandruff actives. Thus, according to another aspect, there is provided an anti-dandruff composition comprising from about 0.01% to about 5%, preferably form about 0.5% to about 2% of chitosan by weight of the composition as the active anti-dandruff agent. In some systems, however, it may be beneficial to use a combination of the chitosan composition with a traditional anti-dandruff agent such as, for example, zinc pyridinethione (ZPT). Thus, according to another aspect, there is provided an anti-dandruff composition comprising the chitosan composition and a further anti-dandruff agent, especially zinc pyridinethione.

Shampoos comprising the chitosan compositions of the invention may comprise the following ingredients:

Detersive Surfactant

The shampoo compositions for use herein contain from 8% to 40% by weight, of detersive surfactant, preferably from 10% to 30%, more preferably from 12% to 25%. Included among the detersive surfactant hereof is an anionic detersive surfactant component. The compositions hereof can additionally contain nonionic and amphoteric surfactants, and mixtures thereof. The anionic detersive surfactant component will generally be present at a level of from 5%, by weight of the composition, preferably at least 8%, more preferably at least 12%.

Anionic Surfactant

The compositions hereof will preferably comprise alkyl sulfate, alkyl ethoxylated sulfate, or a mixture thereof. These materials have the respective formulae $ROSO_3M$ and $RO(C_2H_4O)_xSO_3M$, wherein R is alkyl or alkenyl of from 8 to 30 carbon atoms, x is 1 to 10, and M is H or a salt-forming cation such as ammonium, alkanolamine containing $C_1$–$C_3$ alkyl groups such as triethanolamine, and monovalent and polyvalent metals such as the alkaline and alkaline earth metals. Preferred metals include sodium, potassium, magnesium, and calcium. The cation M, of the anionic surfactant should preferably be chosen such that the anionic surfactant component is water soluble. Solubility of anionic surfactants, in general, will depend upon the particular anionic surfactants and cations chosen.

As an aid to determining appropriate mixtures of anionic surfactants, the anionic surfactants should be chosen such that the Krafft temperature is 15° C. or less, preferably 10° C. or less, more preferably 0° C. or less. It is also preferred that the anionic surfactant be soluble in the composition hereof. Preferably, R has from 10 to 18 carbon atoms in both the alkyl and alkyl ethoxylated sulfates. The alkyl ethoxylated sulfates are typically made as condensation products of ethylene oxide and monohydric alcohols having from 8 to 24 carbon atoms. The alcohols can be derived from fats, e.g., coconut oil, palm kernel oil, or tallow, or can be synthetic. Such alcohols are preferably reacted with 1 to 10, more preferably from 1 to 4, most preferably from 2 to 3.5, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from 12 to 16 carbon atoms and an average degree of ethoxylation of from 1 to 4 moles of ethylene oxide.

The sulfate surfactant is preferably comprised of a combination of ethoxylated and nonethoxylated sulfates. The weight ratio of alkyl sulfate to alkyl ethoxylated sulfate is preferably from 4:1 to 1:10, more preferably from 2:1 to 1:8, even more preferably from 1:1 to 1:5, most preferably from 1:2 to 1:4. Weight ratios as described above are preferred for their ability to provide optimum combinations of lather, cleaning, and particulate anti-dandruff agent performance. Alkyl sulfates can provide excellent cleaning and lather performance. Alkyl ethoxylated sulfates can provide excellent cleaning performance, are mild to the skin, and can enhance deposition of traditional anti-dandruff agents relative to alkyl sulfates.

A preferred type of anionic surfactant, especially for use in combination with anionic sulfate surfactants, are the N-acyl amino acid surfactants. N-acyl amino acid surfactants, for purposes hereof, include N-acyl hydrocarbyl acids and salts thereof, such as those represented by Formula III, as follows: wherein $R^1$ is a $C_8$–$C_{24}$ alkyl or alkenyl radical, preferably $C_{10}$–$C_{18}$; $R^2$ is —H, $C_1$–$C_4$ alkyl, phenyl, or —$CH_2COOM$, preferably $C_1$–$C_4$ alkyl, more preferably $C_1$–$C_2$ alkyl; $R^3$ is —$CR^4_2$— or $C_1$–$C_2$ alkoxy, wherein each $R^4$ independently is —H or $C_1$–$C_6$ alkyl or alkylester, and n is from 1 to 4, preferably 1 or 2; and M is H or a cation as previously defined, preferably an alkali metal such as sodium or potassium.

A wide variety of N-acyl acid surfactants and their synthesis are described in *Anionic Surfactants, Part II, Surfactant Science Series*, Vol. VII, edited by Wamer M. Linfield, Marcel Dekker, Inc. (New York and Basel), 1976; pp 581–617.

Especially preferred are N-acyl sarcosinates, and acids thereof. Specific examples include lauroyl sarcosinate, myristoyl sarcosinate, cocoyl sarcosinate, and oleoyl sarcosinate, preferably in their sodium and potassium salt forms.

For the purposes of the surfactants described herein, it should be understood that the terms "alkyl" or "alkenyl" include mixtures of radicals which may contain one or more intermediate linkages such as ether or polyether linkages or non-functional substituents such as hydroxyl or halogen radicals wherein the radical remains of hydrophobic character.

Anionic detersive surfactants also include aliphatic sulfonates, such as the water-soluble salts of the organic, sulfuric acid reaction products of the general formula:

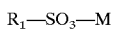

$R_1$—$SO_3$—M wherein $R_1$ is chosen from the group consisting of a straight or branched chain, saturated aliphatic hydrocarbon radical having from 8 to 24, preferably 12 to 18, carbon atoms; and M is a cation, as previously described. Examples are the salts of an organic sulfuric acid reaction product of a hydrocarbon of the methane series, including iso-, neo-, and n-paraffins, having 8 to 24 carbon atoms, preferably 12 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12}$–$C_{18}$ paraffins (e.g. normal and secondary paraffins).

Additional examples of anionic detersive surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other synthetic anionic detersive surfactants of this variety are set forth in U.S. Pat. Ser. No. 2,486,921, U.S. Pat. Ser. Nos. 2,486,922 and U.S. Pat. Ser. No. 2,396,278.

Still other anionic detersive surfactants are in the class designated as succinates. This class includes such surface active agents as disodium N-octadecylsulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; dioctyl esters of sodium sulfosuccinic acid.

Other suitable anionic detersive surfactants also include olefin sulfonates having 12 to 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert dilutents, for example, by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having 12 to 24 carbon atoms, preferably 14 to 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A specific alpha-olefin sulfonate mixture of the above type is described more fully in the U.S. Pat. Ser. No. 3,332,880.

Other suitable anionic detersive surfactants are the beta-alkyloxy alkane sulfonates. Many additional synthetic anionic surfactants are described in *McCutcheon's Emulsifiers and Detergents*, 1989 Annual, published by M. C. Publishing Co. Also U.S. Pat. Ser. No. 3,929,678, discloses many other anionic as well as other surfactant types.

Preferred anionic detersive surfactants for use in the present shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric Surfactant

Amphoteric surfactants can optionally be used in the shampoo compositions. Examples of amphoteric surfactants which can be used herein include those which are broadly described as derivatives of aliphatic secondary and tertiary amines in which the aliphatic radical can be straight or branched chain and wherein one of the aliphatic substituents contains from 8 to 18 carbon atoms and one contains an anionic water solubilizing group, e.g., carboxy, sulfonate, sulfate, phosphate, or phosphonate.

The amphoteric surfactant hereof includes the imidazolinium amphoteric surfactants. Suitable materials of this type are marketed under the tradename MIRANOL and are understood to comprise a complex mixture of species, and can exist in protonated and non-protonated species depending upon pH.

Preferred amphoteric surfactants are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Specific commercial products providing the imidazolinium derivative component of the present compositions include those sold under the trade names MIRANOL (RTM) C2M CONC. N.P., MIRANOL (RTM) C2M CONC. O.P., MIRANOL (RTM) C2M SF, MIRANOL (RTM) CM SPECIAL, MIRANOL (RTM) ULTRA (Miranol, Inc.); ALKATERIC (RTM) 2CIP (Alkaril Chemicals); AMPHOTERGE (RTM) W-2 (Lonza, Inc.); MONATERIC (RTM) CDX-38, MONATERIC (RTM) CSH-32 (Mona Industries); REWOTERIC (RTM) AM-2C (Rewo Chemical Group); and SCHEROTERIC (RTM) MS-2 (Scher Chemicals).

Amphoteric surfactants also include aminoalkanoates of the formula

$$R-NH(CH_2)_nCOOM$$

and iminodialkanoates of the formula:

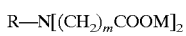
$$R-N[(CH_2)_mCOOM]_2$$

and mixtures thereof, wherein n and m are numbers from 1 to 4, R is $C_8$–$C_{22}$ alkyl or alkenyl, and M is hydrogen or a cation as described above. Examples of such amphoteric surfactants include n-alkylaminopropionates and n-alkyliminodipropionates. Such materials are sold under the tradename DERIPHAT (RTM) by Henkel and MIRATAINE (RTM) by Miranol, Inc. Specific examples include N-lauryl-beta-amino propionic acid or salts thereof, and N-lauryl-beta-imino-dipropionic acid or salts thereof.

Other amphoteric surfactants that can be used include betaine surfactants.

Nonionic Surfactant

Nonionic detersive surfactants are preferred for use herein due to its compatibility with chitosan. Nonionic surfactants include those broadly defined as compounds produced by the condensation of alkylene oxide groups (hydrophilic in nature) with an organic hydrophobic compound, which may be aliphatic or alkyl aromatic in nature. Examples of preferred classes of nonionic detersive surfactants are:

1. The polyethylene oxide condensates of alkyl phenols, e.g., the condensation products of alkyl phenols having an alkyl group containing from 6 to 20 carbon atoms in either a straight chain or branched chain configuration, with ethylene oxide, the said ethylene oxide being present in amounts equal to from 10 to 60 moles of ethylene oxide per mole of alkyl phenol.
2. Those derived from the condensation of ethylene oxide with the product resulting from the reaction of propylene oxide and ethylene diamine products.
3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.
4. Long chain tertiary amine oxides corresponding to the following general formula:

$$R_1R_2R_3N \rightarrow O$$

wherein $R_1$ contains an alkyl, alkenyl or monohydroxy alkyl radical of from 8 to 18 carbon atoms, from 0 to 10 ethylene oxide moieties, and from 0 to 1 glyceryl moiety, and $R_2$ and $R_3$ contain from about 1 to 3 carbon atoms and from 0 to 1 hydroxy group, e.g., methyl, ethyl, propyl, hydroxyethyl, or hydroxypropyl radicals. the arrow in the formula is a conventional representation of a semipolar bond.

5. Long chain tertiary phosphine oxides corresponding to the following general formula:

RR'R"P→O wherein R contains an alkyl, alkenyl or monohydroxyalkyl radical ranging from 8 to about 18 carbon atoms in chain length, from 0 to 10 ethylene oxide moieties and from 0 to 1 glyceryl moiety and R' and R" are each alkyl or monohydroxyalkyl groups containing from 1 to 3 carbon atoms.

6. Long chain dialkyl sulfoxides containing one short chain alkyl or hydroxy alkyl radical of from 1 to 3 carbon atoms (usually methyl) and one long hydrophobic chain which include alkyl, alkenyl, hydroxy alkyl, or keto alkyl radicals containing from 8 to 20 carbon atoms, from 0 to 10 ethylene oxide moieties and from 0 to 1 glyceryl moiety.

7. Alkyl polysaccharide (APS) surfactants such as the alkyl polyglycosides. Such surfactants are described in U.S. Pat. Ser. No. 4,565,647, which discloses APS surfactants having a hydrophobic group with 6 to 30 carbon atoms and polysaccharide (e.g., polyglycoside) as the hydrophilic group. Optionally, there can be a polyalkyleneoxide group joining the hydrophobic and hydrophilic moieties. The alkyl group (i.e., the hydrophobic moiety) can be saturated or unsaturated, branched or unbranched, and unsubstituted or substituted (e.g., with hydroxy or cyclic rings).

8. Polyethylene glycol (PEG) glyceryl fatty esters, such as those of the formula R(O)OCH$_2$CH(OH)CH$_2$(OCH$_2$CH$_2$)$_n$OH wherein n is from 5 to 200, preferably from 20 to 100, and R is an aliphatic hydrocarbyl having from 8 to 20 carbon atoms.

9. Polyhydroxy fatty acid amides. Polyhydroxy fatty acid amides are disclosed, for example, in G.B-A-809,060, U.S. Pat. Ser. No. 2,965,576, U.S. Pat. Ser. No. 2,703,798 and U.S. Pat. No. 1,985,424.

When used, the optional amphoteric and nonionic surfactants are typically present at levels of from 0.05% to 20%, more typically from 0.1% to 10%, preferably from 0.5% to 5%, although higher or lower levels can be used.

Particulate Anti-dandruff Agent

The shampoo compositions can contain one or more particulate antidandruff agents in addition to the chitosan composition. Particulate antidandruff agents include, for example, sulfur, selenium sulfide, and pyridinethione salts. Preferred are heavy metal salts of 1-hydroxy-2-pyridinethione and selenium disulfide. The particulate antidandruff agents are in crystalline form and are insoluble in the compositions. In general, particulate antidandruff agents are used at levels of about 0.1% to about 5%, preferably from about 0.3% to about 5%, by weight of the composition. The particular amount used is not critical as long as an effective amount is used for controlling dandruff when the composition is used to shampoo the hair in the conventional manner.

Selenium sulfide is a staple item of commerce. Selenium sulfide is generally regarded as a compound having one mole of selenium and two moles of sulfur. However, it may take the form of a cyclic structure, Se$_x$S$_y$, wherein x+y=8. U.S. Pat. Ser. No. 2,694,668, U.S. Pat. Ser. No. 3,152,046, U.S. Pat. Ser. No. 4,089,945 and U.S. Pat. Ser. No. 4,885,107 disclose selenium disulfide as an active ingredient in antidandruff shampoo compositions.

Selenium sulfide (selenium disulfide) preferably has an average particle size of less than about 15 μm, more preferably less than about 10 μm. These measurements can be made using a forward laser light scattering device (e.g., a Malvern 3600 particle size analyser).

If used, selenium sulfide is typically present at a level of from about 0.1% to about 5.0%, preferably from about 0.3% to about 2.5%, more preferably from about 0.5% to about 1.5%, by weight of the composition.

Preferred pyridinethione antidandruff agents are water insoluble 1-hydroxy-2-pyridinethione salts. Preferred salts are formed from heavy metals such as zinc, tin, cadmium, magnesium, aluminium and zirconium. The most preferred metal herein is zinc. The most preferred active is the zinc salt of 1-hydroxy-2-pyridinethione, often referred to as zinc pyridinethione (ZPT). Other cations such as sodium may also be suitable. These types of antidandruff agents are well known in the art. Particularly preferred are those 1-hydroxy-2-pyridinethione salts in platelet particle form, wherein the particles have an average size of up to about 20 microns, preferably up to about 8 microns, most preferably up to about 5 microns. The pyridinethione salts are generally used at a level of from about 0.1% to about 3%, preferably about 0.3% to about 2%, by weight of the shampoo composition.

Other particulate antidandruff actives include sulfur. Sulfur is typically used as an antidandruff agent at a level of from about 1% to about 5%, more preferably from about 2% to about 5%, by weight of the composition. Antidandruff actives in soluble form are also suitable for use herein, especially Ketoconazole (cis-1-acetyl-4-[4-[[2-(2,4-dichlorophenyl)-2-(1H-imidazol-1-ylmethyl)-1,3-dioxolan-4-yl]methoxy]phenyl]piperazine).

Suspending Agent

The present compositions may include a crystalline suspending agent. Other suspending agents useful for suspending particulate antidandruff agents (or other materials) and for thickening the compositions can optionally be used.

The crystalline suspending agent should be used at an effective level for suspending the particulate antidandruff agent. The suspension should, in general, be stable for at least one month at ambient temperature. Longer term shelf stability such as at least three months, preferably six months, most preferably at least about twenty-four months, is preferred. In general, the compositions hereof can comprise from about 0.5% to about 10%, by weight, of a crystalline suspending agent or combination thereof. The crystalline suspending agent is preferably present in the shampoo compositions hereof at a level of about 0.5% to about 5%, more preferably about 1% to about 4%, most preferably about 1% to about 3%.

Preferred crystalline suspending agents are acyl derivatives and amine oxides, especially acyl derivatives, expecially those which can be solubilized in a premix solution and then be recrystallized upon cooling. These materials will comprise long chain (e.g., C$_8$–C$_{22}$ preferably C$_{14}$–C$_{22}$, more preferably C$_{16}$–C$_{22}$) aliphatic groups, i.e., long chain acyl derivative materials and long chain amine oxides, as well as mixtures of such materials. Included are ethylene glycol long chain esters, alkanol amides of long chain fatty acids, long chain esters of long chain fatty acids, glyceryl long chain esters, long chain esters of long chain alkanolamides, and long chain alkyl dimethyl amine oxides, and mixtures thereof.

Examples of crystalline suspending agents are described in U.S. Pat. No. 4,741. Suitable suspending agents for use herein include ethylene glycol esters of fatty acids preferably having from about 14 to about 22 carbon atoms, more preferably 16–22 carbon atoms. More preferred are the ethylene glycol stearates, both mono and distearate, but particularly the distearate containing less than about 7% of the mono stearate. Other suspending agents include alkanol amides of fatty acids, preferably having from about 16 to about 22 carbon atoms, more preferably about 16 to 18 carbon atoms. Preferred alkanol amides are stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate); glyceryl esters (e.g., glyceryl distearate) and long chain esters of long chain alkanol amides (e.g., stearamide diethanolamide distearate, stearamide monoethanolamide stearate). Ethylene glycol esters of long chain carboxylic acids, long chain amine oxides, and alkanol amides of long chain carboxylic acids, in addition to the preferred materials listed above, may be used as suspending agents.

Suspending agents also include long chain amine oxides such as alkyl ($C_{16}$–$C_{22}$) dimethyl amine oxides, e.g., stearyl dimethyl amine oxide. If the compositions contain an amine oxide or a long chain acyl derivative which is a surfactant, the suspending function could also be provided by such amine oxide or acyl derivative, provided at least a portion of them are present in crystalline form, and additional suspending agent may not be needed.

Other long chain acyl derivatives that can be used include N,N-dihydrocarbyl ($C_{12}$–$C_{22}$, preferably $C_{16}$–$C_{18}$) amido benzoic acid and soluble salts thereof (e.g., Na and K salts), particularly N,N-di($C_{16}$–$C_{18}$, and hydrogenated tallow) amido benzoic acid species of this family, which are commercially available from Stepan Company (Northfield, Ill., USA).

The crystalline suspending agent serves to assist in suspending the particulate antidandruff agent, or other particulate matter or emulsions of insoluble fluids, in the shampoo compositions hereof, and may give pearlescence to the product.

The crystalline suspending agent can be incorporated into the shampoos hereof by solubilizing it into a solution containing water and the anionic sulfate surfactant at a temperature above the melting point of the suspending agent. The suspending agent is then recrystallized, typically by cooling the solution to a temperature sufficient to induce crystallization.

Optional suspending agent thickeners, and viscosity modifiers, etc., when used are in general at a level of from about 0.01% to about 10%, most commonly from about 0.02% to about 5.0% by weight of the total composition. In general, the level of optional suspending agent and other viscosity modifiers should preferably be as low as possible to achieve the benefit for which the material is added.

Optional suspending agents that can be used include polymeric thickeners, such as carboxyvinyl polymers. Preferred carboxyvinyl polymers are copolymers of acrylic acid crosslinked with polyallylsucrose as described in U.S. Pat. No. 2,798,053. These polymers are provided by B.F. Goodrich Company as, for example, Carbopol 934, 940, 941, and 956.

A carboxyvinyl polymer is an interpolymer of a monomeric mixture comprising a monomeric olefinically unsaturated carboxylic acid, and from about 0.01% to about 10% by weight of the total monomers of a polyether of a polyhydric alcohol, which polyhydric alcohol contains at least four carbon atoms to which are attached at least three hydroxyl groups, the polyether containing more than one alkenyl group per molecule. Other monoolefinic monomeric materials may be present in the monomeric mixture if desired, even in predominant proportion. Carboxyvinyl polymers are substantially insoluble in liquid, volatile organic hydrocarbons and are dimensionally stable on exposure to air.

Preferred polyhydric alcohols used to produce carboxyvinyl polymers include polyols selected from the class consisting of oligosaccharides, reduced derivatives thereof in which the carbonyl group is converted to an alcohol group, and pentaerythritol; more preferred are oligosaccharides, most preferred is sucrose. It is preferred that the hydroxyl groups of the polyol which are modified be etherified with allyl groups, the polyol having at least two allyl ether groups per polyol molecule. When the polyol is sucrose, it is preferred that the sucrose have at least about five allyl ether groups per sucrose molecule. It is preferred that the polyether of the polyol comprise from about 0.01% to about 4% of the total monomers, more preferably from about 0.02% to about 2.5%.

Preferred monomeric olefinically unsaturated carboxylic acids for use in producing carboxyvinyl polymers used herein include monomeric, polymerizable, alpha-beta monoolefinically unsaturated lower aliphatic carboxylic acids; more preferred are monomeric monoolefinic acrylic acids.

Preferred carboxyvinyl polymers used herein have a molecular weight of at least about 750,000; more preferred are carboxyvinyl polymers having a molecular weight of at least about 1,250,000; most preferred are carboxyvinyl polymers having a molecular weight of at least about 3,000,000. Other materials can also be used as optional suspension agents include those that can impart a gel-like viscosity to the composition, such as water soluble or colloidally water soluble polymers like cellulose ethers (e.g., hydroxyethyl cellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Another type of suspending agent that can be used is xanthan gum. Shampoo compositions utilizing xanthan gum as a suspending agent for the silicone hair conditioning component are described in U.S. Pat. No. 4,788,006. Kelco, a Division of Merck & Co., Inc. offers xanthan gum as KeltrolR.

Water

The shampoo compositions herein will comprise from about 40% to about 89%, preferably from about 50% to about 85%, more preferably from about 60% to about 80%, by weight, of water.

The pH of the compositions hereof is not generally critical and may be in the range of from 2 to about 10, preferably from about 3 to about 9, more preferably from about 4 to about 8, most preferably from about 5.5 to about 7.5.

Optional Ingredients

The shampoo compositions used herein may optionally include, for example, preservatives such as benzyl alcohol, methyl paraben, propyl paraben and imidazolidinyl urea; silicone hair conditioning agents; organic hair conditioning materials selected from the group consisting of hydrocarbon fluids and fatty esters; cationic conditioning agents, including both cationic conditioning surfactants and cationic conditioning polymers; quaternary polymeric foam boosters, such as Polyquatemium 10, preferably from about 0.01% to about 0.2%, by weight of the composition; fatty alcohols; block polymers of ethylene oxide and propylene oxide such as Pluronic F88 offered by BASF Wyandotte; sodium chloride, sodium sulfate; ammonium xylene sulfonate; propylene glycol; polyvinyl alcohol; ethyl alcohol; pH adjusting agents such as citric acid, succinic acid, phosphoric acid, sodium hydroxide, sodium carbonate, etc.; perfumes; and dyes. These optional ingredients are typically used at levels of from about 0.01% to about 10% of the composition. This list of optional ingredients is not meant to be exclusive, and other optional components can be utilized.

The chitosan compositions are especially beneficial for reducing hair damage in hair colouring and other hair treatments, such as permanent waving, involving the use of hydrogen peroxide. In order to provide the consumer with the hair colour and intensity of shade desired, a very complex chemical process is utilised. The hair dyeing molecules are typically produced from the reaction of at least one oxidative colouring agent with an oxidising agent which are formed in situ on the hair of consumers and typically in an aggressive environment at about pH 10 and in the presence of an alkalising agent. Moreover, this process is repeated regularly by the consumer in order maintain the desired hair colour and intensity of the hair colour shade and ensure continuous, even coverage of the hair including coverage of new hair growth. The chemistry involved in the hair dyeing process may result in some damage to the hair which is permanent. Damaging effects include tangling, brittleness and dryness. These effects can be reduced to a large extent by the use of the chitosan compositions as part of shampoos, conditioners or leave-on-products such as hair tonics or leave-on-conditioners. Without being bound by theory, it is believed that the chitosan can act as chelating agent for copper and other transition metals, avoiding the build-up of these metals on the hair. These metals appear to catalyse unwanted free-radical side-reactions of oxidizing chemicals, causing damage to the hair.

The chitosan compositions also provides skin care benefits due to its anti-microbial, moisturizing and improved film formation properties, furthermore, it can improve the skin compatibility with cosmetic products. Thus, according to another aspect there is provided the use of the chitosan compositions for skin care including providing skin moisturizing and bacterial control. In yet another aspect there is provided a skin care composition inclusive of moisturizing cream, anti-aging cream, revitalizing cream, cleansing cream and tonics comprising the chitosan composition and a carrier suitable for use in a skin care composition.

The chitosan compositions also provide moisturizing benefits, skin health enhancement and odour control benefits when forming part of personal cleansing compositions such as for example shower gels and bar soaps. The incorporation of chitosan compositions in personal cleansing products allows the user to deliver cleaning agents and skin care agents in a single step.

The anti-microbial and absorbency properties of the chitosan compositions make it very suitable for use in odour control. Thus according to another aspect there is provided the use of the chitosan compositions for odour control. There is also provided an odour control composition inclusive of deodorants and anti-perspirant comprising the chitosan composition and a carrier suitable for use in odour control.

Due to its improved anti-microbial properties the chitosan composition may be used for wound care including providing healing promotion, microbial contamination prevention, blood gellation and scarring prevention. The compositions can be especially useful for the treatment of burmts due to the anti-microbial and film forming properties. Thus, according to another aspect there is provided a wound care composition comprising the chitosan composition and a carrier suitable for use in a wound care composition.

Another use of the chitosan composition due to its superior control of gelling and mal-odour and absorbing properties, is blood management including menstrual fluid gellation, retention in pad cores, accidental blood spillage control, post-traumatic control of bleeding and surgical blood loss control. Thus, according to another aspect there is provided a blood management composition comprising the chitosan composition and a carrier suitable for use in a blood management composition. The compositions can be especially useful for control of toxic shock syndrome, related to tampon use, due to the efficiency of the chitosan against Staphylococcus aureus. In yet another aspect there is provided a sanitary composition comprising the chitosan composition and a carrier suitable for use in a sanitary composition.

Due to the improve anti-microbial, substantivity, film forming and solubility properties of the chitosan compositions as well as the excellent safety profile and natural origin the chitosan compositions are suitable for use in oral and denture care including improvement of general gum and teeth health, treatment of halitosis and gingivitis, stain reduction, and for providing anti-caries, anti-plaque and anti-calculus benefits, in humans or other animals. It has been found that the chitosan compositions used herein have improved effect on the inhibition of cariogenic bacteria such as *Streptococcus mutans* this effect combined with its pH buffering capacity make the chitosan compositions very effective in prevention of dental caries. It has also been found that the chitosan compositions used herein have improved effect on the inhibition of hydrogen sulphide and volatile odiferous organosulphade compounds produced by salivary micro-organisms, being therefore very effective for breath odour improvement. Additionally, the excellent substantive and film forming properties of the chitosan compositions, make them very effective for plaque and tartar control. Furthermore, the network of chitosan fibres can be very useful for the release of other actives such as Triclosan (2,4,4'-trichloro-2'-hydroxy-diphenyl ether), either in solubilised form or in the form of small nanoparticles, which can be entrained into the interstitial space. Oral and denture care compositions comprising the chitosan compositions can be in the form of toothpastes, gels, mouth rinses, mouth sprays, lozenges, tooth whitenings, denture cleansings, dental floss, dental tape and chewing gums comprising one of the chitosan compositions and a carrier or substrate suitable for use in an oral care composition.

The choice of a carrier or substrate to be used is basically determined by the way the composition is to be introduced into the oral cavity. If a toothpaste (including tooth gels, etc.) is to be used, then a "toothpaste carrier" is chosen as disclosed in, e.g., U.S. Pat. No. 3,988,433, to Benedict (e.g., abrasive materials, sudsing agents, binders, humectants, flavoring and sweetening agents, etc.). If a mouth rinse is to be used, then a "mouth rinse carrier" is chosen, as disclosed in, e.g., U.S. Pat. No. 3,988,433 to Benedict (e.g., water, flavoring and sweetening agents, etc.). Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,083,955, to Grabenstetter et al.; if a chewing gum is to be used, then a "chewing gum carrier" is chosen, as disclosed in, e.g., U.S. Pat. No. 4,083,955, to Grabenstetter et al., (e.g., gum base, flavoring and sweetening agents). If a sachet is to be used, then a "sachet carrier" is chosen (e.g., sachet bag, flavoring and sweetening agents). If a subgingival gel is to be used (for delivery of actives into the periodontal pockets or around the periodontal pockets), then a "subgingival gel carrier" is chosen as disclosed in, e.g. U.S. Pat. No. 5,198,220, Damani and U.S. Pat. No. 5,242,910, Damani. Carriers suitable for the preparation of compositions of the present invention are well known in the art. Their selection will depend on secondary considerations like taste, cost, and shelf stability, etc.

Preferred oral or denture compositions for use herein are in the form of dentifrices, such as toothpastes and tooth gels. Components of such toothpaste and tooth gels generally include one or more of a dental abrasive (from about 10% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion), and an anticalculus agent (from about 0.1% to about 13%).

Other preferred oral or denture compositions are non-abrasive gels, including subgingival gels, which generally include a thickening agent (from about 0.1% to about 20%), a humectant (from about 10% to about 55%), a flavoring agent (from about 0.04% to about 2%), a sweetening agent (from about 0.1% to about 3%), a coloring agent (from about 0.01% to about 0.5%), water (from about 2% to about 45%), and may comprise an anticaries agent (from about 0.05% to about 0.3% as fluoride ion), and an anticalculus agent (from about 0.1% to about 13%).

Other preferred oral or denture compositions are mouthwashes, including mouth sprays. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion), and an anticalculus agent (from about 0.1% to about 3%).

Other preferred oral or denture compositions are dental solutions. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%). Chewing gum compositions typically include one or more of a gum base (from about 50% to about 99%), a flavoring agent (from about 0.4% to about 2%) and a sweetening agent (from about 0.01% to about 20%).

Types of carriers or substrate oral care excipients which may be included in compositions of the present invention are:

Abrasives

Dental abrasives useful in the topical, oral carriers of the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510. Suitable resins include, for example, melamines, phenolics, ureas, melamine-ureas, melamine-formaldehydes, urea-formaldehyde, melamine-urea-formaldehydes, cross-linked epoxides, and cross-linked polyesters. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in U.S. Pat. No. 3,538,230 and U.S. Pat. No. 3,862,307. Preferred are the silica xerogels marketed under the trade name "Syloid" by the W.R. Grace & Company, Davison Chemical Division. Also preferred are the precipitated silica materials such as those marketed by the J. M. Huber Corporation under the trade name, Zeodent®, particularly the silica carrying the designation Zeodent 119®. The types of silica dental abrasives useful in the toothpastes of the present invention are described in more detail U.S. Pat. No. 4,340,583. The abrasive in the toothpaste compositions described herein is generally present at a level of from about 6% to about 70% by weight of the composition. Preferably, toothpastes contain from about 10% to about 50% of abrasive, by weight of the composition.

A particularly preferred precipitated silica is the silica disclosed in U.S. Pat. No. 5,603,920, U.S. Pat. No. 5,589,160, U.S. Pat. No. 5,658,553 and U.S. Pat. No. 5,651,958.

Mixtures of abrasives can be used. The total amount of abrasive in dentifrice compositions of the subject invention preferably range from about 6% to about 70% by weight; toothpastes preferably contain from about 10% to about 50% of abrasives, by weight of the composition. Solution, mouth spray, mouthwash and non-abrasive gel compositions of the subject invention typically contain no abrasive.

Sudsing Agents (Surfactants)

Suitable sudsing agents are those which are reasonably stable and form foam throughout a wide pH range. Sudsing agents include nonionic, anionic, amphoteric, cationic, zwitterionic, synthetic detergents, and mixtures thereof. Many suitable nonionic and amphoteric surfactants are disclosed by U.S. Pat. No. 3,988,433 and U.S. Pat. No. 4,051,234, and many suitable nonionic surfactants are disclosed by U.S. Pat. No. 3,959,458.

a) Nonionic and Amphoteric Surfactants

Nonionic surfactants which can be used in the oral or dental care compositions can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials.

The amphoteric surfactants useful for use herein can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed.

The present composition can typically comprise a nonionic, amphoteric, or combination of nonionic and amphoteric surfactant each at a level of from about 0.025% to about 5%, preferably from about 0.05% to about 4%, and most preferably from about 0.1% to about 3%.

b) Anionic Surfactants

Anionic surfactants are preferred for use herein because they can form coacervates with the chitosan. The formed coacervate is very substantive to the tooth surface, providing two main benefits. Firstly, prolongs the time that the chitosan is on the tooth and therefore the anti-bacteria benefits and secondly, the chitosan can enhance the delivery of other actives.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. The present composition typically comprises an anionic surfactant at a level of from about 0.025% to about 9%, preferably from about 0.05% to about 7%, and most preferably from about 0.1% to about 5%.

Fluoride Ions

The compositions used herein may also incorporate free fluoride ions. Preferred free fluoride ions can be provided by sodium fluoride, stannous fluoride, indium fluoride, and sodium monofluorophosphate. Sodium fluoride is the most preferred free fluoride ion. U.S. Pat. No. 2,946,725 and U.S. Pat. No. 3,678,154 disclose such salts as well as others.

The present composition may contain from about 50 ppm to about 3500 ppm, and preferably from about 500 ppm to about 3000 ppm of free fluoride ions.

Thickening Agents

In preparing toothpaste or gels, it is necessary to add some thickening material to provide a desirable consistency of the composition, to provide desirable chitosan release characteristics upon use, to provide shelf stability, and to provide stability of the composition, etc. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

A preferred class of thickening or gelling agents includes a class of homopolymers of acrylic acid crosslinked with an alkyl ether of pentaerythritol or an alkyl ether of sucrose, or carbomers. Carbomers are commercially available from B.F. Goodrich as the Carbopol® series. Particularly preferred carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. No. 5,198,220, U.S. Pat. No. 5,242,910 and U.S. Pat. No. 4,443,430.

Thickening agents in an amount from about 0.1% to about 15%, preferably from about 2% to about 10%, more preferably from about 4% to about 8%, by weight of the total toothpaste or gel composition, can be used. Higher concentrations can be used for chewing gums, lozenges (including breath mints), sachets, non-abrasive gels and subgingival gels.

Humectants

Another optional component of the oral or denture compositions is a humectant. The humectant serves to keep such compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use herein include edible polyhydric alcohols such as glycerin, sorbitol, xylitol, butylene glycol, polyethylene glycol, and propylene glycol, especially sorbitol and glycerin.

Flavoring and Sweetening Agents

Flavoring agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition preferably contains from about 0.1% to about 10% of these agents, preferably from about 0.1% to about 1%, by weight of the composition.

In addition to flavoring and sweetening agents, coolants, salivating agents, warming agents, and numbing agents can be used as optional ingredients herein. These agents are present in the compositions at a level of from about 0.001% to about 10%, preferably from about 0.1% to about 1%, by weight of the composition.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levo-rotatory isomers of these compounds and racemic mixtures thereof. TK-10 is described in U.S. Pat. No. 4,459,425. WS-3 and other agents are described in U.S. Pat. No. 4,136,163.

Preferred salivating agents of the present invention include Jambu® manufactured by Takasago. Preferred warming agents include capsicum and nicotinate esters, such as benzyl nicotinate. Preferred numbing agents include benzocaine, lidocaine, clove bud oil, and ethanol.

Anticalculus Agent

The oral or denture care compositions can also include an anticalculus agent, preferably a pyrophosphate ion source which is from a pyrophosphate salt. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na4P_2O_7$), and tetrapotassium pyrophosphate ($K_4P_2O_7$) in their unhydrated as well as hydrated forms are the preferred species.

The pyrophosphate salts are described in more detail in Kirk & Othmer, *Encyclopedia of Chemical Technology*, Third Edition, Volume 17, Wiley-Interscience Publishers (1982).

Optional agents to be used in place of or in combination with the pyrophosphate salt include such known materials as synthetic anionic polymers, including polyacrylates and copolymers of maleic anhydride or acid and methyl vinyl ether (e.g., Gantrez), as described, for example, in U.S. Pat. No. 4,627,977; as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

Alkali Metal Bicarbonate Salt

The oral or denture care compositions may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

Miscellaneous Carriers

Water employed in the preparation of commercially suitable oral compositions should preferably be of low ion content and free of organic impurities. Water generally comprises from about 5% to about 70%, and preferably from about 20% to about 50%, by weight of the composition herein. These amounts of water include the free water which is added plus that which is introduced with other materials, such as with sorbitol.

Titanium dioxide may also be added to the present composition, preferably in levels of from about 0.25% to about 5% by weight of the dentifrice compositions. Titanium dioxide is a white powder which adds opacity to the compositions. Additional antimicrobial antiplaque agents can also by optionally present in oral compositions. Such agents may include, but are not limited to, triclosan, 5-chloro-2-(2,4-dichlorophenoxy)-phenol, as described in *The Merck Index*, 11th ed. (1989), pp. 1529 (entry no. 9573) in U.S. Pat. No. 3,506,720, and in EP-A-0,251,591; chlorhexidine (*Merck Index*, no. 2090), alexidine (*Merck Index*, no. 222; hexetidine (*Merck Index*, no. 4624); sanguinarine (*Merck Index*, no. 8320); benzalkonium chloride (*Merck Index*, no. 1066); salicylanilide (*Merck Index*, no. 8299); domiphen bromide (*Merck Index*, no. 3411); cetylpyridinium chloride (CPC) (*Merck Index*, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and analogs and salts of the above antimicrobial antiplaque agents. If present, the antimicrobial antiplaque agents generally comprise from about 0.1% to about 5% by weight of the compositions of the present invention.

Anti-inflammatory agents may also be present in the oral compositions of the present invention. Such agents may include, but are not limited to, non-steroidal anti-inflammatory agents such as aspirin, ketorolac, flurbiprofen, ibuprofen, naproxen, indomethacin, aspirin, ketoprofen, piroxicam and meclofenamic acid, and mixtures thereof. If present, the anti-inflammatory agents generally comprise from about 0.001% to about 5% by weight of the compositions of the present invention. Ketorolac is described in U.S. Pat. No. 5,626,838.

Other optional agents include synthetic anionic polymeric polycarboxylates being employed in the form of their free acids or partially or preferably fully neutralized water soluble alkali metal (e.g. potassium and preferably sodium) or ammonium salts and are disclosed in U.S. Pat. No. 4,152,420, U.S. Pat. No. 3,956,480 U.S. Pat. No. 4,138,477, U.S. Pat. No. 4,183,914, and U.S. Pat. No. 4,906,456. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez (AN 139 (M.W. 500,000), A.N. 119 (M.W. 250,000) and preferably S-97 Pharmaceutical Grade (M.W. 70,000), of GAF Corporation.

The oral or denture care composition can also optionally comprise selective H-2 antagonists including compounds disclosed in U.S. Pat. No. 5,294,433.

In the case of oral care compositions for animals, especially pets, the carrier or substrate may be chosen according to the kind of pet considered, for instance, in the case of dogs the chitosan compositions can be applied to the surface of dog toys or dog chews, this would allow for the chitosan to stay in contact with the dog oral cavity for a length of time sufficient to provide halitosis as well as general gum and teeth health benefits. The chitosan can be applied to the toy or chew as a permanent coating or alternatively the chitosan composition can be sold to the pet owner together with a carrier or substrate, in the form of toy, chew or other substrate, that the owner can dip into the composition as required.

In the case of cats, the oral compositions can be delivered by coating dry pellets or cat biscuits with the chitosan compositions.

According to another aspect, the use of the chitosan compositions for in situ film formation on a substrate to provide surface protection, surface modification, antibacterial properties and enhanced shine is provided. The superior film formation properties of the chitosan compositions seem to be due to the structure of the network of nano-chitosan fibres. In yet another aspect, there is provided a hard surface treatment composition comprising one of the chitosan compositions and a carrier suitable for use in a hard surface composition.

The chitosan compositions also provide fabric benefits such as malodour control (due to its anti-microbial properties) during wearing and enhanced wearing comfort (due to its softening properties). The compositions can be applied to the fabric in the form of a permanent treatment or provisional treatment by means of softener, easy-ironing or two-in-one laundry composition.

According to another aspect, there is provided the use of the chitosan compositions for controlled release of hydrophobic or hydrophilic materials, including water, skin moisturizers, proteins, enzymes, perfumes, triglycerides, waxes, fatty acids, sebum and mixtures thereof. The chitosan amino group can be Schiff complexed with perfume aldehyde, providing useful fragrance effects including high substantivity and long lasting fragrance and also providing deodorancy effect. The chitosan-aldehyde Schiff Base can be used for example as part of a fine-fragrance composition or as part of a detergent or laundry conditioner composition. The Schiff Base can be hydrolysed by contact with the user's skin slowly releasing the perfume.

It has been found that the chitosan compositions have improved bio-availability and are easily metabolised by plants. Advantages of these properties can be taken in the case of foliar or soil application and are reflected in an increased growth, accelerated flowering, and immunisation against bacterial, fungal and viral pathogens as well as improved health and vigor of plants. Additionally, the chitosan compositions have enhanced chelating abilities for control or release of transition metals, providing a carbon source for biochemical synthesis at the same time as being a vehicle to deliver assimilable metal nutrients. Thus, according to another aspect, there is provided the use of chitosan compositions for plant care including delivery of micro-nutrient metals, especially iron, manganese, copper and zinc, in natural chelated form, by foliar or soil administration and development of immunization in plants against fungal, viral and bacterial pathogens. The chitosan compositions can be directly applied to the plants by foliar spraying, through irrigation or any other known method or alternatively it can be delivered as part of a plant care composition. Thus, according to another aspect, there is provided a plant care composition inclusive of health compositions, growth and flowering enhancer compositions, nutritional compositions, leaf cleansing compositions and leaf shine compositions comprising the chitosan composition and a carrier suitable for use in a plant care composition.

Advantages are also found when the chitosan compositions are used as soil conditioner, playing a soil pathogen control role. It is believed that the chitosan compositions used herein boost beneficial chitosanolitic bacteria which destroy pathogenic flingis such as Botrytis sp. Another advantage of the chitosan compositions used herein for plant care is the enhanced plant phyto-compatibility due to the aqueous nature of the compositions, increased solubility at physiological pH and the absence of acid or other phytotoxic process modifiers. Thus, according to another aspect, there is provided the use of the chitosan compositions for soil conditioning including boosting soil symbiotic bacteria levels and reducing levels of pathogenic fungi. There is also provided, a soil conditioning composition comprising one of the chitosan compositions and a carrier suitable for use in a soil conditioning composition.

It has also been found that the chitosan compositions deliver protection benefits for seed, grain, fruit and food. The chitosan compositions provide seed and grain fangal protection and additional germination boosting and promotion of vigorous early growth after germination. It also prevents premature spoil of fruit and has excellent preservative properties for food applications. Thus, according to another aspect there is provided the use of the chitosan compositions for seed, grain, fruit or food protection. There is also provided a seed, grain, fruit or food protection composition comprising the chitosan composition and a carrier suitable for use in a seed, grain, fruit or food composition.

The plant care compositions for use herein can be used for ornamental plants, including home, garden and greenhouse plants and for agriculture crops. Health compositions, growth and flowering enhancing compositions and nutritional compositions preferably comprise the following ingredients:

Macronutrients

Macronutrients are essential to plant nutrition and growth, to flowering, to flower setting, to fruit setting, to saturation, etc. The most important macronutrients are N, P and K, also Ca, S and Mg are also important. They can be delivered to plants through different compounds as described herein below.

Nitrogen: ammonium nitrate, monoammonium phosphate, ammonium phosphate sulfate, ammonium sulfate, ammonium phosphatenitrate, diammonium phosphate, ammoniated single superphosphate, ammoniated triple super-phosphate, nitric phosphates, ammonium chloride, aqua ammonia, ammonia-ammonium nitrate solutions, calcium ammonium nitrate, calcium nitrate, calcium cyanamide, sodium nitrate, urea, urea-formaldehyde, urea-ammonium nitrate solution, nitrate of soda potash, potassium nitrate, amino acids, proteins, nucleic acids, etc.

Phosphorous: superphosphate (single, double and/or triple), phosphoric acid, ammonium phosphate, ammonium phosphate sulfate, ammonium phosphate nitrate, diammonium phosphate, ammoniated single superphosphate, ammoniated single superphosphate, ammoniated triple superphosphate, nitric phosphates, potassium pyrophosphates, sodium pyrophosphate, nucleic acid phosphates, etc.

Potassium: potassium chloride, potassium sulfate, potassium gluconate, sulfate of potash magnesia, potassium carbonate, potassium acetate, potassium citrate, potassium hydroxide, potassium manganate, potassium phosphate, potassium molybdate, potassium thiosulfate, potassium zinc sulfate, etc.

Calcium: calcium ammonium nitrate, calcium nitrate, calcium cyanamide, calcium acetate, calcium acetylsalicylate, calcium borate, calcium borogluconate, calcium carbonate, calcium chloride, calcium citrate, calcium ferrous citrate, calcium glycerophosphate, calcium lactate, calcium oxide, calcium pantothenate, calcium proprionate, calcium saccharate, calcium sulfate, calcium tartrate, etc.

Magnesium: magnesium oxide, dolomite, magnesium acetate, magnesium benzoate, magnesium bisulfate, magnesium borate, magnesium chloride, magnesium citrate, magnesium nitrate, magnesium phosphate, magnesium salicylate, magnesium sulfate S-ammonium sulfate, ammonium phosphate sulfate, calcium sulfate, potassium sulfate, magnesium sulfate, sulfuric acid, cobalt sulfate, copper sulfate, ferric sulfate, ferrous sulfate, sulfur, cysteine, methionine, etc.

Micronutrient

The most important micronutrients are Zn, Fe and Mn. They can be delivered to plants through different compounds as described herein below.

Zinc: zinc oxide, zinc acetate, zinc bensoate, zinc chloride, zinc citrate, zinc nitrate, zinc salicylate, ziram, etc.

Iron: ferric chloride, ferric citrate, ferric fructose, ferric glycerophosphate, ferric nitrate, ferric oxide (saccharated), ferrous chloride, ferrous citrate ferrous fumarate, ferrous gluconate, ferrous succinate, etc.

Manganese: manganese acetate, manganese chloride, manganese nitrate, manganese phosphate Copper: copper acetate, copper butyrate, copper chloride, copper citrate, copper gluconate, copper glycinate, copper nitrate, copper salicylate, etc.

Boron: calcium borate, potassium borohydride, borax, boron trioxide, potassium borotartrate, potassium tetraborate, sodium borate, sodium borohydride, sodium tetraborate, etc.

Molybdenum: molybdic acid, calcium molybdate, potassium molybdate, sodium molybdate, etc.

Cobalt: cobaltic acetate, cobaltous acetate, cobaltous chloride, cobaltous potassium sulfate, cobaltous sulfate, etc.

Vitamin/Cofactor Component

The most important are folic acid, biotin, pantothenic acid, nicotinic acid, riboflavin and thiamine.

Thickeners

The compositions herein preferably also include a thickener. By thickener is meant a component which has thickening properties, that is a compound which produces compositions with a higher viscosity in the presence of the thickener than in the absence of the thickener. They help to disperse the chitosan. Suitable thickener agents for use herein are: i) polymeric thickeners, such as polycarboxylate synthetic polymer preferably cross-linked and with a molecular weight at least about 500,000; ii) natural gums, such as xanthan gum, locust bean gum, guar gum and the like; iii) semi-synthetic thickeners such as the cellulosic type thickeners: hydroxymethyl and hydroxyethyl cellulose and iv) mixtures thereof. A preferred thickener is Natrosol. Natrosol is trademark of Hercules, Inc. of Wilmington, Del. Natrosol is a hydroxycellulose ether adhesive thickener.

Non-phytotoxic Soap

The plant care compositions used herein can also include non-phytotoxic fatty acid salts or soap. The soap has insecticidal properties as well as cleansing properties. Regarding the insectidal soap either one, or preferably, a mixture of fatty acid salts are normally employed. Preferred fatty acid salts are those having between eight and twenty carbon atoms in a straight chain structure with the alpha carbon comprising a monocarboxylic acid moiety esterified, preferably completely, with a monovalent metal such as sodium or potassium. Alkanol ammonia and ammonia can also be used as counter-ion for the salts. This group of fatty acid salts are known to have insecticidal activity, and have been used for many years in the control of pestiferous arthropods. Fatty acid soap materials are widely commercially available. They can be produced from coconut oils, comprising predominantly a mixture of laurate (C-12) and myristate (C-14). They are also derived from various plant and animal sources. The preferred fatty acids are those having eight to eighteen carbon atoms including caprylate, laurate, myristate, palmitate, oleate, linoleate and stearate. Most preferred are unsaturated, eighteen carbon atom salts such as alkali metal oleate and linoleate, and saturated eight to twelve carbon atom salts such as mixtures of alkali metal caprylate, pelargonate,.caprate, undecylinate and laurate.

Other ingredients useful for plant compositions herein are fragrance with insect repellent properties as described in copending U.S. Ser. No. 01/17243, pages 5 and 6 and physically active insecticidal material as also described in copending U.S. Ser. No. 01/17243, page 10.

Another field of application of the chitosan compositions is in water and beverage purification due to its superior flocculation and especially heavy metal sequestration properties (it is more weight effective than other forms of chitosan), particularly superior control of transition metals in the presence of competing alkali earth metals, as well as superior bio-compatibility. Thus, according to another aspect, there is provided the use of the chitosan compositions as flocculant for water and beverage purification. According to another aspect, there is provided the use of the chitosan compositions as metal sequestrant. The chitosan acts as a selective sequestrant, being specific for the sequestration of transition metals (e.g., Cu, Fe) and not for the sequestration of alkaline metals (e.g., Ca, Mn), therefore being of value in hard water situations. In yet another aspect, there is provided a water-purification composition comprising the chitosan composition and a carrier suitable for use in a water-purification composition. The composition being adequate for in home use or for industrial use.

Finally, due to the superior bio-compatibility of the chitosan composition, according to another embodiment, there is provided the use of the chitosan composition as vehicle for drug delivery. According to another aspect, there is also provided a pharmaceutical composition comprising the chitosan composition and a carrier suitable for use in a pharmaceutical composition.

EXAMPLES

Example 1

A process to produce the composition of the invention is described herein below. The process comprises two-main steps:

a) Dissolution of Chitosan in an Acidic Solution:

1980 g of deionised water are weighed into 10 l stainless steel vessel of 22 cm diameter (T). Stirring is started using and overhead stirrer (Heidolph RZR 2041) with 4-pitched-blade impeller of 12 cm diameter (D) (D/T=0.55). Stirring is carried out at 200 rpm (1.3 m/s tip speed). 20 g of chitosan, sourced from Primex having a molecular weight of approximately 150 kDa and degree of acetylation of 15–20% are added slowly to the vessel, whilst stirring, avoiding contact with the vessel walls or the impeller shaft. Before proceeding to the next stage the mixture is stirred for 5 minutes to allow suspended chitosan to wet. Then, 333 g of an 18% by weight of a lactic acid aqueous solution are added to the vessel to solubilise the chitosan. The resulting mixture is stirred at 200 rpm and maintained for further 10 minutes to allow the chitosan to be fully solubilised in the acidic solution. The resulting solution is filtered through a single 60 cm×60 cm layer of mercerised cotton (pre-rinsed in deionised water) fitted in a 6 liters polypropylene Buchner funnel, and the filtrate is collected in a 5 liters clean Buchner flask. This stage removes any insoluble contaminants.

b) Neutralization of the Resulting Acidic Solution:

The filtered acidic chitosan solution is returned to the 10 l stainless steel vessel and stirred at 200 rpm. A 1.5% by weight sodium hydroxide aqueous solution is added to the acidic chitosan solution at a rate of 20 ml/min via a peristaltic pump (Watson Marlow 205U) from 2 kg reservoir of 1.5% by weight sodium hydroxide solution. Addition is carried out at 200 rpm until the mixture reaches a pH of 6.85 or 6.90. The vessel content is then mixed at high speed, 600 rpm, for 15 minutes. The stirring speed is reduced to 200 rpm–250 rpm and 1.5% by weight sodium hydroxide is added at a reduced rate of about 12 ml/min until pH 7.45–7.50 reached. The vessel content is mixed at high speed, ~600rpm (3.8 m/s tip speed) for 15 minutes. Then the stirring speed is reduced to 200 rpm–250 rpm for 5 minutes to remove air generated in high speed mixing stage. The vessel content is filtered through a single 60 cm×60 cm layer of mercerised cotton (pre-rinsed in deionised water) fitted in a 6 liters polypropylene Buchner funnel to remove waste liquid. Nanochitosan is insoluble and collects on the cotton layer. Vacuum may be used to speed up removal of waste liquid. Nanochitosan is washed with 3×1000 ml aliquots of deionised water. Excess water is removed by vacuum filtration. The washed nanochitosan material is weighed into a tared 1000 ml container. If preservation is required, 1 g of 20% chlorhexidine digluconate is added to container. Deionised water is added to obtain 1000 g total and produce 1 kg of a solution comprising 2% by weight of nano-sized chitosan.

Example 2

Example 1 is repeated using hydrochloric acid instead of lactic acid.

Example 3

The first step of the process is carried out as in Example 1, the second step involves the use of two sodium hydroxide solutions of different concentrations. The acidic chitosan solution formed in step a) is neutralized with a 1.5% by weight sodium hydroxide solution until a pH of about 5.5 is reached, then a 0.15% by weight sodium hydroxide solution is used for further neutralization. The neutralization is carried out in the same way as in Example 1.

Examples 4–6

As Examples 1 to 3 but using a high speed, during the high shear stirring steps, of 1000 rpm instead of 600 rpm.

The chitosan composition obtained according to Examples 1 to 6 is used in the compositions of Examples 7 to 16. The percent by weight given in Examples 7 to 16 refers to active chitosan.

Examples 7–10

The following compositions exemplify shampoos of the present invention. They provide excellent anti-dandruff benefits and hair damage reduction after colouring, dyeing, bleaching and permanent waving.

| Component | Example Number | | | |
|---|---|---|---|---|
| (%, by weight, of composition) | 7 | 8 | 9 | 10 |
| Sodium Laureth-3 Sulfate | 13.5 | 15.0 | 14.25 | 13.5 |
| Ammonium Lauryl Sulfate | 4.5 | 5.0 | 4.75 | 4.5 |
| Coconut ($C_{12}$–$C_{14}$) Fatty Alcohol | 0.17 | 0.17 | 0.17 | 0.17 |
| Sodium Lauryl Sarcosinate[4] | 1.5 | 1.5 | 1.25 | 1.5 |
| Sodium Sulfate | 0.88 | 0.88 | 0.88 | 0.88 |
| Polyquaternium 10[1] | 0.025 | 0.025 | 0.025 | 0.025 |
| Ethylene Glycol Distearate | 1.5 | 1.5 | 1.5 | 1.5 |
| Dimethicone[2] | 0.50 | 0.0 | 0.0 | 0.5 |
| Perfume Solution | 0.65 | 0.65 | 0.65 | 0.65 |
| DMDM Hydantoin | 0.20 | 0.20 | 0.20 | 0.20 |
| PEG 600[3] | 0.125 | 0.125 | 0.125 | 0.125 |
| Ammonium Chloride | 0.06 | 0.06 | 0.06 | 0.06 |
| Zinc Pyridinethione | | 0.5 | 0.2 | |
| Chitosan | 1.0 | 0.5 | 0.4 | 1.0 |
| Color Solution (ppm) | 10 | 10 | 10 | 10 |
| Water and Minors | | q. s. to 100% | | |

[1]UCARE Polymer JR-30M, commercially available from Union Carbide Corporation.
[2]A 40(gum)/60(fluid) weight ratio blend of SE-76 dimethicone gum available from General Electric Silicones Division and a dimethicone fluid having a viscosity of 350 $mm^2s^{-1}$ (centistokes).
[3]Polyethylene (600) glycol, a polymer of ethylene oxide having an average degree of polymerization of about 600.
[4]Available under the tradename Hamposyl L-30 from Hampshire Chemical Corp. as a 30% active solution.

Example 11

The following composition exemplifies a conditioner of the present invention. It provides hair damage reduction during colouring, dyeing, bleaching and permanent waving.

| Ingredient | Wt. % |
|---|---|
| Purified Water | 88.50 |
| L-Gultamic Acid | 0.560 |
| SAPDMA[1] | 1.600 |
| Cetyl Alcohol | 2.000 |
| Stearyl Alcohol | 3.600 |
| Methyl Paraben | 0.200 |
| Propyl Paraben | 0.100 |
| Phenoxy Ethanol | 0.300 |
| Sodium chloride | 0.010 |
| Benzyl Alcohol | 0.400 |
| Chitosan | 2.000 |
| Citric acid | 0.130 |
| Perfume | 0.400 |
| Dimethicone | 0.200 |
| Total | 100.00 |

[1]Stearamidopropyl Dimethylamine

Example 12

The following single phase dentifrice composition is made by conventional processes by mixing the following ingredients:

| Ingredient | Wt. % |
|---|---|
| Water | 62.277 |
| Sodium Chlorite | 2.750 |

-continued

| Ingredient | Wt. % |
|---|---|
| Sodium Fluoride | 0.243 |
| Chitosan | 1.00 |
| Hydrated Silica | 25.000 |
| Xanthan Gum | 0.600 |
| Carbomer 956[1] | 0.200 |
| Sodium alkyl sulfate (27.9% Sol'n) | 4.000 1.000 |
| Titanium Dioxide | 0.130 |
| Sodium Saccharin | 1.000 |
| Flavor | 1.800 |
| Sodium Hydroxide (50% Sol'n) | |
| Total | 100.00 |

[1]Available from B. F. Goodrich.

Example 13

The following single phase mouthwash composition is made by conventional processes by mixing the following ingredients:

| Ingredient | Wt. % |
|---|---|
| Water | 98.80 |
| Chitosan | 0.1 |
| Sodium Chlorite | 0.25 |
| Sodium Carbonate | 0.53 |
| Sodium Bicarbonate | 0.42 |
| Total | 100.00 |

Example 14

| Non-Abrasive Gel | |
|---|---|
| Ingredient | Weight % |
| Sodium Chlorite (80%) | 2.75 |
| Chitosan | 1.0 |
| Carbopol 956[1] | 8.00 |
| Sodium Bicarbonate | 0.84 |
| Sodium Hydroxide (50% Solution) | 8.00 |
| Water | QS 100% |

[1]Available from B. F. Goodrich.

For the preparation of the non-abrasive gel the Carbopol is dispersed in water. Thereafter, the sodium hydroxide is added and mixed. Then the sodium bicarbonate. Finally, the chitosan composition is added and mixed.

Example 15

A chewing gum with the following formulation is prepared.

| Ingredient | % |
|---|---|
| Glycerin | 8.0 |
| Xylitol | 17.0 |
| Hydrated silica | 10.0 |
| Chitosan | 1.00 |
| Gum base (eg Prestige-PL, Cafosa) | 27.0 |
| Hydrogenated starch hydrolisate | 8.0 |
| Mannitol | 5.0 |
| Flavour | 1.6 |
| Aspartame | 0.2 |
| Spray dried flavour | 0.15 |
| Sucrose polycottonseedate | 5.0 |
| Sorbitol (70%) | qs 100 |

Example 16

The following plant care composition is prepared:

| Ingredients | Source | Concentration (% W/W) |
|---|---|---|
| Nitrogen (N) | Urea | 0.020 |
| Phosphorus (P) | Monobasic potassium phosphate | 0.020 |
| Potassium (K) | | 0.025 |
| Boron (B) | Boric Acid | <0.001 |
| Manganese (Mn) | Manganese (II) chloride.4H2O | <0.001 |
| Molybdate (Mo) | Sodium Molybdate | 0.003–0.01 |
| Iron (Fe) | Iron (II) chloride.4H2O | 0.01–0.1 |
| Magnesium (Mg) | EDTA magnesium disodium hydrate | <0.001 |
| Nickel (Ni) | Nickel (II) nitrate.6H2O | <0.001 |
| Zinc (Zn) | Zinc Sulphate.7H2O | <0.001 |
| Calcium (Ca) | EDTA calcium disodium hydrate | 0.001 |
| Proxel GXL | | 0.01 |
| Hydroxyethylcellulose | | 0.500 |
| Chitosan | | 0.05 |
| Water | | ~97.0 |
| Perfume | | 0.005 |
| Colour | Naphthol Green B | 0.0001 |
| Sodium (Na) | | 0.001 |
| Chloride (Cl) | | <0.001 |
| Sulphate (SO4$^{2-}$) | | <0.001 |

The plant care composition is applied to Cyclamen plants and the growing and flowering of the plants is evaluated against control plants that are only treated with water. The plants treated with chitosan grow and flower faster and also look much healthier than the control plants.

What is claimed:

1. A composition comprising chitosan in the form of a network of nano-sized fibers having an interstitial space as determined by cryogenic transmission electron microscopic imaging of at least about 80%.

2. The composition of claim 1, wherein said nano-size fibers have an average length ranging from about 50 nm to about 100 nm, a width ranging from about 5 nm to about 30 nm, and a thickness ranging from about 1 nm to about 10 nm, as determined by cryogenic transmission electron microscopic imaging.

3. The composition of claim 1, wherein said chitosan has a water retention value of at least about 3000 percent.

4. The composition of claim 1, wherein said composition is selected from the group consisting of hair care compositions, skin care compositions, personal cleansing compositions, odor control compositions, oral care compositions, denture care compositions, plant care compositions, water purification compositions, and combinations thereof.

5. The composition of claim 4, wherein said hair care composition further comprises from at least about 0.01% by weight to at least about 5% by weight an active anti-dandruff agent.

6. The composition of claim 4, wherein said skin care composition is selected from the group consisting of moisturizing creams, anti-aging creams, revitalizing creams, cleansing creams, cleansing tonics, and combinations thereof.

7. The composition of claim 4, wherein said oral care composition is selected from the group consisting of toothpastes, gels, toothpowders, mouth rinses, mouth sprays, lozenges, tooth whitenings, denture cleansings, chewing gums, and combinations thereof.

8. A composition comprising chitosan in the form of a network of nano-sized fibers, wherein said chitosan has a water retention value of at least about 3000 percent.

9. The composition of claim 8, wherein said composition is selected from the group consisting of hair care compositions, skin care compositions, personal cleansing compositions, odor control compositions, oral care compositions, denture care compositions, plant care compositions, water purification compositions, and combinations thereof.

10. The composition of claim 9, wherein said skin care composition is selected from the group consisting of moisturizing creams, anti-aging creams, revitalizing creams, cleansing creams, cleansing tonics, and combinations thereof.

11. The composition of claim 9, wherein said oral care composition is selected from the group consisting of toothpastes, gels, toothpowders, mouth rinses, mouth sprays; lozenges, tooth whitenings, denture cleansings, chewing gums, and combinations thereof.

12. The composition of claim 8, wherein said chitosan has a surface area of at least about 100 $m^2/g$, a degree of crystallinity below about 1%, and is soluble in aqueous solutions having a pH between about 1 and about 6.3.

13. A process for making a chitosan composition in the form of a network of nano-sized fibers comprising the steps of:
  (a) dissolving chitosan in aqueous acid to form an aqueous chitosan solution;
  (b) partially neutralizing said aqueous chitosan solution with a neutralizing agent;
  (c) precipitating said aqueous chitosan solution with said neutralizing agent to form a chitosan suspension; and,
  (d) homogenizing said chitosan suspension with a high shear forming a homogenized chitosan suspension thereby.

14. The process of claim 13, wherein said aqueous chitosan solution has a concentration of chitosan in the range of from about 0.5% by weight to about 2% by weight and said aqueous chitosan solution has a pH in the range of from about 1 to about 5.

15. The process of claim 14, comprising the step of, prior to step (b), filtering said aqueous chitosan solution.

16. The process of claim 13, wherein said neutralizing agent is an aqueous solution comprising from at least about 0.05% by weight to about 3% by weight of an alkali selected from the group consisting of alkali metal hydroxides, ammonium hydroxide, organic bases thereof, and mixtures thereof.

17. The process of claim 16, wherein said chitosan suspension, after step (b), has a pH in the range of from about 6.7 to about 7.1.

18. The process of claim 13, wherein during step (d), said chitosan suspension has a Reynolds number ranging from about 8,000 to about 20,000, and wherein said chitosan suspension is homogenized at a speed of rotation of from at least about 500 rpm for at least about 15 minutes.

19. The process of claim 13, wherein said step (b) comprises:
  (i) partially neutralizing said aqueous chitosan solution to a pH ranging from about 5.3 to about 6.7 with a neutralizing agent, said partial neutralization comprising a first stage; and
  (ii) partially neutralizing said aqueous chitosan solution with a neutralizing agent that is about five times more dilute than the neutralizating agent utilized in step (i).

20. The process of claim 19, further comprising the steps of:
  (e) neutralizing said homogenized chitosan suspension with an aqueous solution of said neutralizing agent forming a neutralized chitosan suspension, said aqueous solution of said neutralizing agent comprising from about 0.05% by weight to about 0.5% by weight of an alkali selected from the group consisting of metal hyroxde, ammonium hyroxide, mixtures thereof, and combinations thereof;
  (f) homogenizing said neurelized chitosan suspension at a high shear; and, wherein after step (e), said pH of said suspension ranges from at least about 7.2 to at least about 7.6.

* * * * *

UNITED STATES PATENT AND TRADEMARK OFFICE
CERTIFICATE OF CORRECTION

PATENT NO. : 6,638,918 B2
DATED : October 28, 2003
INVENTOR(S) : Davison et al.

It is certified that error appears in the above-identified patent and that said Letters Patent is hereby corrected as shown below:

Column 16,
Line 62, "Polyquatemium" should be -- Polyquaternium --.

Column 26,
Line 15, "fangal" should be -- fungal --.

Column 34,
Line 40, "hyroxde" should be -- hydroxide --.
Line 42, "neurelized" should be -- neutralized --.

Signed and Sealed this

Seventeenth Day of January, 2006

JON W. DUDAS
*Director of the United States Patent and Trademark Office*